United States Patent [19]

Ehrenfreund et al.

[11] Patent Number: 4,677,212
[45] Date of Patent: Jun. 30, 1987

[54] INTERMEDIATE 1,2-BENZOXATHIIN DERIVATIVES

[75] Inventors: Josef Ehrenfreund, Allschwil; Werner Föry, Basel; Willy Meyer, Riehen; Werner Töpfl, Dornach, all of Switzerland

[73] Assignee: Ciba-Geigy Corporation, Ardsley, N.Y.

[21] Appl. No.: 658,003

[22] Filed: Oct. 4, 1984

Related U.S. Application Data

[63] Continuation-in-part of Ser. No. 512,091, Jul. 8, 1983, Pat. No. 4,634,465.

[30] Foreign Application Priority Data

Jul. 16, 1982 [CH] Switzerland ............ 4357/82

[51] Int. Cl.⁴ .................. C07D 327/06
[52] U.S. Cl. .................. 549/15
[58] Field of Search .................. 549/15

[56] References Cited

FOREIGN PATENT DOCUMENTS 1238158 7/1971 United Kingdom ............ 549/15

*Primary Examiner*—Henry R. Jiles
*Assistant Examiner*—J. G. Mullins
*Attorney, Agent, or Firm*—Edward McC. Roberts; Kevin T. Mansfield

[57] ABSTRACT

The invention relates to N-phenylsulfonyl-N'-pyrimidinylureas and N-phenylsulfonyl-N-triazinylureas of the general formula

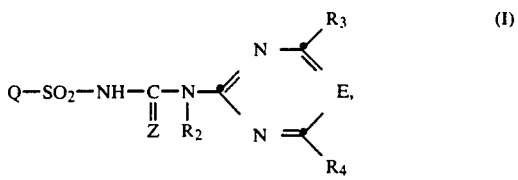

wherein
Q is selected from a radical

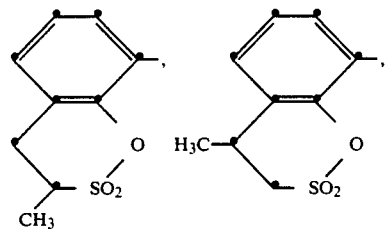

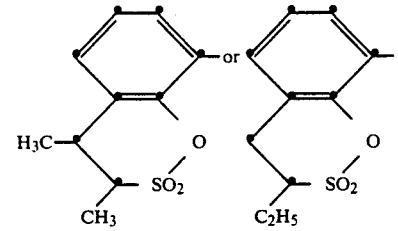

Z is oxygen or sulfur,
E is nitrogen or =CH—,
$R_2$ is hydrogen, $C_1$–$C_4$ alkyl or $C_1$–$C_3$ alkoxy, and
$R_3$ and $R_4$, each independently of the other, are hydrogen, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkyl, $C_2$–$C_5$ alkoxyalkoxy or —$NR_5R_6$, wherein $R_5$ and $R_6$ are hydrogen or $C_1$–$C_4$ alkyl, and to the salts of these compounds with amines, alkali metal bases or alkaline earth metal bases or with quaternary ammonium bases. These compounds have good pre- and postemergence selective herbicidal and growth regulating properties.

5 Claims, No Drawings

INTERMEDIATE 1,2-BENZOXATHIIN DERIVATIVES

CROSS REFERENCE TO RELATED APPLICATIONS

This is a continuation-in-part of application Ser. No. 512,091, filed on July 8, 1983, now U.S. Pat. No. 4,634,465.

The present invention relates to novel N-phenylsulfonyl-N'-pyrimidinylureas and N-phenylsulfonyl-N'-triazinylureas having herbicidal and growth regulating properties, to the production thereof, to compositions containing them, and to the use thereof for controlling weeds, in particular selectively, in crops of useful plants, or for regulating and inhibiting plant growth. The invention also relates to novel fused phenylsulfonylisocyanates, phenylsulfonylthioisocyanates, phenylsulfonylcarbamates, phenylsulfonamides and phenylsulfonyl chlorides.

The N-phenylsulfonyl-N'-pyrimidinylureas and N-phenylsulfonyl-N'-triazinylureas of this invention, and the salts thereof, have the general formula I

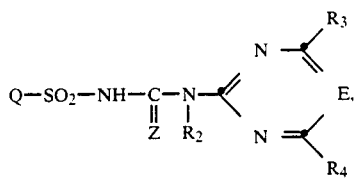
(I)

wherein
Q is selected from a radical

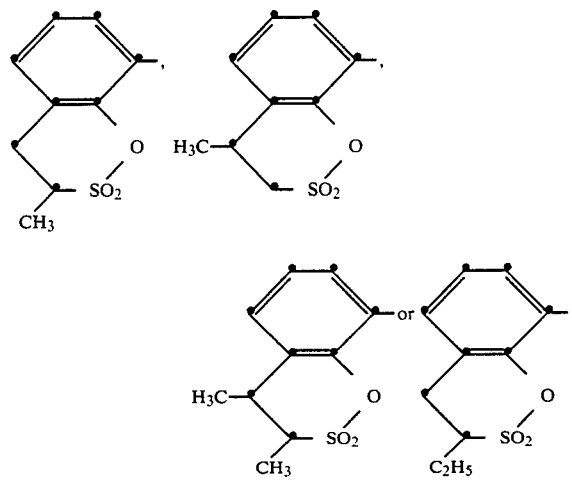

Z is oxygen or sulfur,
E is nitrogen or =CH—,
$R_2$ is hydrogen, $C_1$–$C_4$ alkyl or $C_1$–$C_3$ alkoxy, and
$R_3$ and $R_4$, each independently of the other, are hydrogen, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkyl, $C_2$–$C_5$ alkoxyalkoxy or —$NR_5R_6$, wherein $R_5$ and $R_6$ are hydrogen or $C_1$–$C_4$ alkyl.

Herbicidally active ureas, triazines and pyrimidines are generally known in the art. Arylsulfamoyl-heterocyclyl-aminocarbamoyl compounds with herbicidal and plant growth-regulating action have recently been described e.g. in Netherlands patent specification No. 121 788, U.S. Pat. No. 4,127,405 and in European patent application No. 44 807, 44 808 and 51 465.

In the above definitions, alkyl denotes straight-chain or branched alkyl, e.g. methyl, ethyl, n-propyl, isopropyl, or the four butyl isomers. Alkoxy denotes methoxy, ethoxy, n-propoxy, isopropoxy, the four butoxy isomers, n-amyloxy, isoamyloxy, 2-amyloxy or 3-amyloxy, with methoxy, ethoxy or isopropoxy being preferred.

Alkylthio is e.g. methylthio, ethylthio, n-propylthio, isopropylthio, n-butylthio or n-pentylthio, with methylthio and ethylthio being preferred.

Alkylsulfinyl is e.g. methylsulfinyl, ethylsulfinyl, n-propylsulfinyl and n-butylsulfinyl, with methylsulfinyl and ethylsulfinyl being preferred.

Alkylsulfonyl is e.g. methylsulfonyl, ethylsulfonyl or n-propylsulfinyl, with methylsulfonyl and ethylsulfonyl being preferred.

Halogen in the above definitions, as well as moiety of haloalkyl, haloalkoxy and haloalkylthio, is fluorine, chlorine and bromine, with fluorine and chlorine being preferred.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of formula I are those in which either
(a) Q is

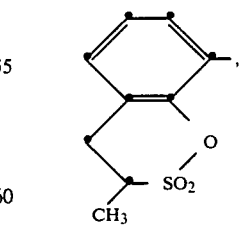

(b) Z is oxygen, or
(c) $R_2$ is hydrogen, or
(d) $R_3$ and $R_4$, independently of each other, are $C_1$–$C_4$ alkyl, $C_1$–$C_4$ alkoxy, di($C_1$–$C_4$)alkylamino, $C_1$–$C_4$ haloalkoxy or halogen, and together contain not more than 4 carbon atoms.

Further preferred subgroups comprise those compounds of formula I in which Z is oxygen, $R_2$ is hydrogen, and each of $R_3$ and $R_4$ independently of the other is $C_1$-$C_4$ alkyl, $C_1$-$C_4$ alkoxy, di($C_1$-$C_4$)alkylamino, $C_1$-$C_4$ haloalkoxy or halogen, and together contain not more than 4 carbon atoms.

Particularly preferred groups of compounds of formula I comprise those compounds in which Z is oxygen, $R_2$ is hydrogen, each of $R_3$ and $R_4$ independently of the other is $C_1$-$C_4$ alkyl, $C_1$-$C_4$ alkoxy, di($C_1$-$C_4$)alkylamino, $C_1$-$C_4$ haloalkoxy or halogen, and together contain not more than 4 carbon atoms, and Q is

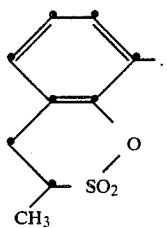

Preferred individual compounds are:

N-(3,4-dihydro-2,2-dioxo-3-methyl-1,2-benzoxathiin-8-ylsulfonyl)-N'-(4-methoxy-6-methylpyrimidin-2-yl)urea, and N-(3,4-dihydro-2,2-dioxo-3-methyl-1,2-benzoxathiin-8-yl-sulfonyl)-N'-4,6-dimethoxypyrimidin-2-yl)-urea.

The process for preparing the compounds of formula I is carried out in an inert organic solvent.

A first process for the preparation of the compounds of formula I comprises reacting a phenylsulfonamide of the formula II $$Q-SO_2-NH_2 \quad (II),$$

wherein Q is as defined for formula I, with an N-pyrimidinylcarbamate or N-triazinylcarbamate of the formula III

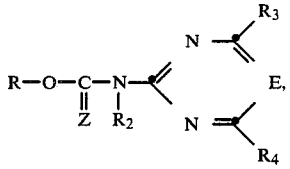

wherein E, $R_2$, $R_3$, $R_4$ and Z are as defined for formula I and R is phenyl, alkyl or substituted phenyl, in the presence of a base.

A second process for obtaining the compounds of formula I comprises reacting a phenylsulfonylisocyanate or phenylsulfonylisothiocyanate of the formula IV $$Q-SO_2-N=C=Z \quad (IV),$$

wherein Q and Z are as defined for formula I, with an aminopyridine or aminotriazine of the formula V

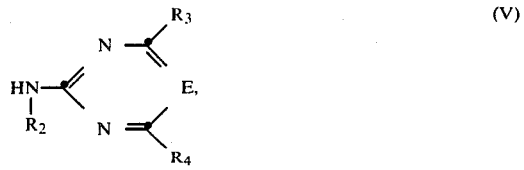

wherein E, $R_2$, $R_3$ and $R_4$ are as defined for formula I, optionally in the presence of a base.

Finally, the compounds of formula I may also be obtained by reacting a N-phenylsulfonylcarbamate of the formula VI

wherein Q and Z are as defined for formula I and R is phenyl, alkyl or substituted phenyl, with an aminopyrimidine or aminotriazine of the formula V above.

If desired, the ureas of formula I can be converted into addition salts with amines, alkali metal hydroxides or alkaline earth metal hydroxides, or with quaternary ammonium bases. This conversion is carried out e.g. by reacting the compounds of formula I with the equimolar amount of a base and removing the solvent by evaporation.

It is convenient to carry out these reactions for obtaining compounds of formula I in aprotic, inert organic solvents.

Examples of such solvents are: benzene, toluene, xylene or cyclohexane, chlorinated hydrocarbons such as methylene chloride, chloroform, carbon tetrachloride, or chlorobenzene; ethers such as diethyl ether, ethylene glycol dimethyl ether, diethylene glycol dimethyl ether, tetrahydrofuran or dioxan; nitriles such as acetonitrile or propionitrile; amides such as dimethylformamide, diethylformamide or N-methylpyrrolidinone.

The reaction temperatures are preferably in the range from $-20°$ to $+120°$ C. The coupling reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst. Preferred bases are tertiary amines such as trimethylamine, triethylamine, quinuclidine, 1,4-diazabicyclo[2.2.2]octane, 1,5-diazabicyclo[4.3.0]-non-5-ene or 1,8-diazabicyclo[5.4.0]undec-7-ene. However, the bases employed may also be inorganic bases, e.g. hydrides such as sodium hydride or calcium hydride, hydroxides such as sodium hydroxide or potassium hydroxide, or bicarbonates such as potassium bicarbonate or sodium bicarbonate.

The final products can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The intermediates of formulae II, IV and VI are novel and have been specially developed for the synthesis of compounds of the formula I. Accordingly, they constitute an object of the present invention.

The novel intermediates of the formula II can be prepared by different methods. For example, the compounds of formula II are obtained by diazotising anilines of formula VII

Q—NH$_2$                                                   (VII), wherein Q is as defined for formula I, and replacing the diazo group with sulfur dioxide, in the presence of a catalyst such as copper chloride, in hydrochloric acid or acetic acid, and reacting the resultant phenylsulfonyl chloride of the formula X

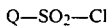

Q—SO$_2$—Cl                                          (X), wherein Q is as defined for formula I, with ammonium hydroxide solution. The corresponding aniline derivatives employed as starting materials are known or they can be prepared by known methods.

Likewise, the compounds of formula II can be obtained by converting a phenylsulfonic acid of the formula VIII

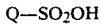

Q—SO$_2$OH                                          (VIII), wherein Q is as defined for formula I, by treatment with a chlorinating agent such as PCl$_5$, POCl$_3$, COCl$_2$ or SOCl$_2$, to the corresponding phenylsulfonyl chloride of the formula X, and reacting this chloride with ammonium hydroxide solution.

The compounds of formula II can also be obtained by treating a benzyl thioether of the formula IX

Q—S—CH$_2$—C$_6$H$_5$                         (IX), wherein Q is as defined for formula I, with chlorine, and reacting the resultant phenylsulfonyl chloride of the formula X with ammonium hydroxide solution. In specific cases, for example where an activated substitution position is available, a direct sulfochlorination of the phenyl nucleus is possible, giving the corresponding phenylsulfonyl chloride by reaction with an excess of chlorosulfuric acid. Correspondingly activated fused benzene derivatives are known, or can be prepared been known processes.

The phenylsulfonylisocyanates of the formula IV, which are also novel, can be obtained by reacting the sulfonamides of the formula II with phosgene, in the presence of butylisocyanate, in a chlorinated hydrocarbon as solvent, at reflux temperature. Similar reactions are described in "Newer Methods of Preparative Organic Chemistry", Vol. VI, 223–241, Academic Press, New York and London.

The isothiocyanates of the formula IV are obtained by treating the sulfonamides of formula II with carbon disulfide and potassium hydroxide and by subsequent reaction of the dipotassium salt with phosgene. Such processes are described in Arch. Pharm. 299, 174 (1966).

The N-phenylsulfonylcarbamates of the formula VI are obtained by reacting the sulfonamides of the formula II with diphenyl carbonate, substituted diphenyl carbonates, or dialkyl carbonates in the presence of a base. Similar processes are described in Japanese patent specification No. 61 169.

The phenylsulfonyl chlorides of the formula X, which are also novel, have likewise been specially developed for the synthesis of the compounds of formula I. Accordingly, they also constitute an object of this invention.

The starting aminopyrimidines and aminotriazines of the formula V, as well as corresponding phenylcarbamates of the formula III, have either long been known or are described in European patent application No. 70 804, or they can be prepared by known methods from compounds disclosed therein.

The compounds of formula I are stable compounds, and no protective measures are required for handling them.

When used in low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used in very low rates of application.

The compounds of formula I have in addition pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whilst vegetative growth is inhibited.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1964.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

Emulsifiable concentrates active ingredient: 1 to 20%, preferably 5 to 10%
surfactant: 5 to 30%, preferably 10 to 20%
liquid carrier: 50 to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 0.5 to 90%, preferably 10 to 80%
surfactant: 0.5 to 20%, preferably 1 to 15%
solid carrier: 5 to 95%, preferably 15 to 90%

Granulates active ingredient: 0.5 to 30%, preferably 3 to 15%
solid carrier: 99.5 to 70%, preferably 97 to 85%.
Whereas commercial products will be preferably formulated as concentrates, the end user will normally employ dilute formulations. The formulations can be diluted to a concentration as low as 0.001%. The rates of application are normally from 0.01 to 10 kg a.i./ha, preferably from 0.025 to 5 kg a.i./ha.

The compositions may also contain further ingredients, such as stabilisers, antifoams, viscosity regulators, binders tackifiers as well as fertilisers or other active ingredients in order to obtain special effects.

PREPARATORY EXAMPLES

Example 1

(a)

6-Bromo-3,4-dihydro-3-methyl-1,2-benzoxathiine 6.7 g of bromide are added dropwise to a mixture of 7.92 g of 3,4-dihydro-2,2-dioxo-3-methyl-1,2-benzoxathiine, 6.5 g of sodium acetate, 0.1 g of iodine and 60 ml of glacial acetic acid, which is then stirred for 24 hours at a temperature of 40° C. The mixture is concentrated and taken up with a mixture of water and ethyl acetate. The organic phase is separated, twice washed with an aqueous solution of sodium hydrogen-carbonate, dried and evaporated. The oily residue is introduced into the following reaction step without further purification operations.

(b)

6-Bromo-3,4-dihydro-2,2-dioxo-3-methyl-1,2-benzoxathiin-8-yl-sulfochloride 8.5 ml of chlorosulfonic acid are added dropwise over 15 minutes at −5° C. to a solution of 4.35 g 6-bromo-3,4-dihydro-3-methyl-1,2-benzoxathiine in 45 ml of chloroform. The mixture is refluxed for 5 hours, cooled to room temperature and poured into ice-water. The organic phase is separated, dried, and concentrated. The oily residue is introduced into the following reaction step without further purification operations.

(c)

6-Bromo-3,4-dihydro-2,2-dioxo-3-methyl-1,2-benzoxathiin-8-yl-sulfonamide 5.6 g of 6-bromo-2,2-dioxo-3-methyl-1,2-benzoxathiin-8-ylsulfochloride are solved in 25 ml of tetrahydrofurane, and the solution is cooled to 0° C. and added dropwise to 30 ml of 25% aqueous ammonia. The reaction mixture is stirred for 3 hours at the same temperature, and poured on a mixture of ice and 5% aqueous hydrochlorid acid. The precipitate is collected and dried at 60° C.

(d)

3,4-Dihydro-2,2-dioxo-3-methyl-1,2-benzoxathiin-8-ylsulfonamide 2,2 g of 6-bromo-3,4-dihydro-2,2-dioxo-3-methyl-1,2-benzoxathiin-8-ylsulfonamide are hydrogenated in the presence of 0.7 g of sodium acetate and 0.3 g of 5% palladium on carbon catalyst at 20° C. and 1 bar in 45 ml of tetrahydrofurane. The catalyst is removed, the solvent evaporated, the residue taken up with a mixture of water and ethyl acetate. The organic phase is separated, washed with a saturated aqueous solution of sodium chloride, dried and concentrated. The residue is crystallised from acetonitrile, affording 3,4-dihydro-2,2-dioxo-3-methyl-1,2-benzoxathiin-8-ylsulfonamide with a melting point of 204°–205° C.

(d)

N-(3,4-Dihydro-2,2-dioxo-3-methyl-1,2-benzoxathiin-8-ylsulfonyl)-N'-(4-methoxy-6-methylpyrimidin-2-yl)urea A mixture of 3.33 g of 3,4-dihydro-2,2-dioxo-3-methyl-1,2-benzoxathiin-8-ylsulfonamide, 1.84 ml of 1,8-diazabicyclo[5.4.0]undec-7-ene, 3.2 g of N-(4-methoxy-6-methylpyrimidin-2-yl)phenylcarbamate and 35 ml of absolute dioxane is stirred for 45 minutes at a temperature of 20° to 25° C. The solvent is destilled off and the oily residue is triturated with ether and 14 ml of 1N hydrochloric acid. The precipitate is separated, washed with water and dried, affording 4.96 g of N-(3,4-dihydro-2,2-dioxo-3-methyl-1,2-benzoxathiin-8-ylsulfonyl)-N'-(4-methoxy-6-methylpyrimidin-2-yl)urea with a melting point of 215°–218° C.

EXAMPLE 2

(a)

N-(3,4-Dihydro-2,2-dioxo-3-methyl-1,2-benzoxathiin-8-ylsulfonyl)-N'-methyl-urea 6.54 ml of 1,8-diazabicyclo[5.4.0]undec-7-ene are added to 12.1 g (0.0436 mole) of 3,4-dihydro-2,2-dioxo-3-methyl-1,2-benzoxathiin-8-ylsulfonamide in dioxane. While cooling with ice, 2.65 ml of methyl isocyanate are added dropwise. The reaction mixture is stirred for 2 hours at 20° to 25° C., then diluted with water, neutralised with 10 ml of 5% sodium carbonate solution, and filtered. Acidification of the filtrate yields 12.0 g (91% of theory) of N-(3,4-dihydro-2,2-dioxo-3-methyl-1,2-benzoxathiin-8-ylsulfonyl)-N'-methylurea.

(b)

3,4-Dihydro-2,2-dioxo-3-methyl-1,2-benzoxathiin-8-ylsulfonylisocyanate 10 g of N-(3,4-dihydro-2,2-dioxo-3-methyl-1,2-benzoxathiin-8-ylsulfonyl)-N'-methylurea are dispersed in 400 ml of absolute chlorobenzene and the dispersion is saturated with phosgene at about 130° C., whereupon a clear solution forms. The solvent is then distilled off in vacuo, with the exclusion of moisture, to give 3,4-dihydro-2,2-dioxo-3-methyl-1,2-benzoxathiin-8-ylsulfonylisocyanate in the form of an oil, which can be used without further purification for obtaining the fused N-phenylsulfonyl-N'-pyrimidinylureas and N-phenylsulfonyl-N'-triazinylureas of the formula I.

The intermediates and final products listed in the following tables are obtained in corresponding manner.

The ring system numbers additionally listed in Table 1 refer only to the fused phenyl ring and are employed for the same substituent in the subsequent tables.

TABLE 1

| | | Q—SO$_2$NH$_2$ | |
|---|---|---|---|
| Compound | Ring system | Q | m.p. [°C.] |
| 1.1 | Q$_1$ | 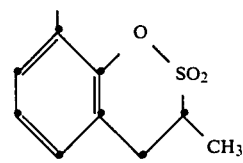 | 186–188 |

TABLE 1-continued

Q—SO$_2$NH$_2$

| Compound | Ring system Q | Q | m.p. [°C.] |
|---|---|---|---|
| 1.2 | Q$_2$ | 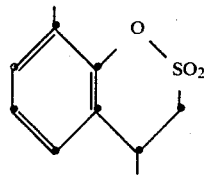 | |
| 1.3 | Q$_3$ | 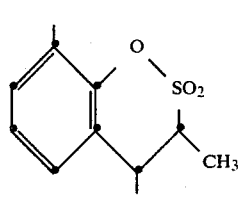 | |
| 1.4 | Q$_4$ | 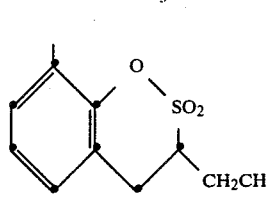 | |

TABLE 2

Q—SO$_2$Cl

| Compound | Q | m.p. [°C.] |
|---|---|---|
| 2.1 | Q$_1$ | oil |
| 2.2 | Q$_2$ | |
| 2.3 | Q$_3$ | |
| 2.4 | Q$_4$ | |

TABLE 3

Q—SO$_2$NCO

| Compound | Q | Physical data |
|---|---|---|
| 3.1 | Q$_1$ | oil |
| 3.2 | Q$_2$ | |
| 3.3 | Q$_3$ | |
| 3.4 | Q$_4$ | |

TABLE 4

Q—SO$_2$—NH—CO—T

| Compound | Q | T | m.p. [°C.] |
|---|---|---|---|
| 4.1 | Q$_1$ | NHCH$_3$ | |
| 4.2 | Q$_2$ | NHC$_4$H$_9$—n | |
| 4.3 | Q$_3$ | NHCH$_3$ | |
| 4.4 | Q$_4$ | NHCH$_3$ | |
| 4.5 | Q$_5$ | NHCH$_3$ | |
| 4.6 | Q$_6$ | NHC$_4$H$_9$—n | |
| 4.7 | Q$_1$ | OC$_6$H$_5$ | |
| 4.8 | Q$_2$ | OC$_6$H$_5$ | |
| 4.9 | Q$_3$ | OC$_6$H$_5$ | |
| 4.10 | Q$_4$ | OC$_6$H$_5$ | |
| 4.11 | Q$_1$ | OCH$_3$ | |
| 4.12 | Q$_2$ | OCH$_3$ | |
| 4.13 | Q$_3$ | OCH$_3$ | |
| 4.14 | Q$_4$ | OCH$_3$ | |
| 4.15 | Q$_1$ | OC$_2$H$_5$ | |
| 4.16 | Q$_2$ | OC$_2$H$_5$ | |
| 4.17 | Q$_3$ | OC$_2$H$_5$ | |
| 4.18 | Q$_4$ | OC$_2$H$_5$ | |

TABLE 5

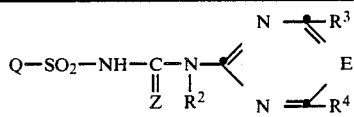

Q has the meanings given in Table 1 for the fused phenyl ring

| Compound | Q | R$^2$ | R$^3$ | R$^4$ | Z | E | m.p. [°C.] |
|---|---|---|---|---|---|---|---|
| 5.1 | Q$_1$ | H | CH$_3$ | OCH$_3$ | O | N | 196–198 |
| 5.2 | Q$_1$ | H | CH$_3$ | CH$_3$ | O | N | |
| 5.3 | Q$_1$ | H | OCH$_3$ | OCH$_3$ | O | N | 129–131 (decomp.) |
| 5.4 | Q$_1$ | H | OCH$_3$ | N(CH$_3$)$_2$ | O | N | 207–209 |
| 5.5 | Q$_1$ | H | CH$_3$ | OCH$_2$CH$_3$ | O | N | 187–189 |
| 5.6 | Q$_1$ | H | OCH$_3$ | OCH$_2$CF$_3$ | O | N | |
| 5.7 | Q$_1$ | H | CH$_2$CH$_3$ | OCH$_3$ | O | N | 103–106 (decomp.) |
| 5.8 | Q$_1$ | H | OCH$_2$CH$_3$ | OCH$_2$CH$_3$ | O | N | 137–140 (decomp.) |
| 5.9 | Q$_1$ | H | CH$_3$ | CH$_3$ | O | CH | 209–210 |
| 5.10 | Q$_1$ | H | CH$_3$ | OCH$_3$ | O | CH | 216–218 |
| 5.11 | Q$_1$ | H | CH$_3$ | OCHF$_2$ | O | CH | 182–184 |
| 5.12 | Q$_1$ | H | OCH$_3$ | OCH$_3$ | O | CH | 202–204 |
| 5.13 | Q$_1$ | H | OCH$_3$ | OCHF$_2$ | O | CH | 105–107 (decomp.) |
| 5.14 | Q$_1$ | H | OCH$_3$ | Cl | O | CH | |
| 5.15 | Q$_1$ | H | OCH$_3$ | F | O | CH | |
| 5.16 | Q$_1$ | H | CH$_2$F | OCH$_3$ | O | CH | |
| 5.17 | Q$_1$ | H | OCH$_3$ | OCF$_2$CHF$_2$ | O | CH | |
| 5.18 | Q$_1$ | H | CH$_3$ | OCF$_2$CHF$_2$ | O | CH | |
| 5.19 | Q$_1$ | CH$_3$ | OCHF$_2$ | OCHF$_2$ | O | CH | 191–193 (decomp.) |
| 5.20 | Q$_1$ | CH$_3$ | OCH$_2$ | OCH$_3$ | O | CH | |
| 5.21 | Q$_1$ | CH$_3$ | OCH$_3$ | CH$_3$ | O | N | |
| 5.22 | Q$_2$ | H | CH$_3$ | OCH$_3$ | O | N | |
| 5.23 | Q$_2$ | H | OCH$_3$ | OCH$_3$ | O | N | |
| 5.24 | Q$_2$ | H | OCH$_3$ | N(CH$_3$)$_2$ | O | N | |
| 5.25 | Q$_2$ | H | OCH$_3$ | OCH$_2$CF$_3$ | O | N | |
| 5.26 | Q$_2$ | H | CH$_3$ | CH$_3$ | O | CH | |
| 5.27 | Q$_2$ | H | OCH$_3$ | CH$_3$ | O | CH | |
| 5.28 | Q$_2$ | H | OCH$_3$ | OCH$_3$ | O | CH | |
| 5.29 | Q$_2$ | H | CH$_3$ | OCHF$_2$ | O | CH | |
| 5.30 | Q$_3$ | H | CH$_3$ | OCH$_3$ | O | N | |
| 5.31 | Q$_3$ | H | OCH$_3$ | OCH$_3$ | O | N | |
| 5.32 | Q$_3$ | H | OCH$_3$ | N(CH$_3$)$_2$ | O | N | |
| 5.33 | Q$_3$ | H | OCH$_3$ | OCH$_2$CF$_3$ | O | N | |
| 5.34 | Q$_3$ | H | CH$_3$ | CH$_3$ | O | CH | |
| 5.35 | Q$_3$ | H | OCH$_3$ | CH$_3$ | O | CH | |
| 5.36 | Q$_3$ | H | OCH$_3$ | OCH$_3$ | O | CH | |
| 5.37 | Q$_3$ | H | CH$_3$ | OCHF$_2$ | O | CH | |
| 5.38 | Q$_4$ | H | CH$_3$ | OCH$_3$ | O | N | |
| 5.39 | Q$_4$ | H | OCH$_3$ | OCH$_3$ | O | N | |
| 5.40 | Q$_4$ | H | OCH$_3$ | N(CH$_3$)$_2$ | O | N | |
| 5.41 | Q$_4$ | H | OCH$_3$ | OCH$_2$CF$_3$ | O | N | |
| 5.42 | Q$_4$ | H | CH$_3$ | CH$_3$ | O | CH | |
| 5.43 | Q$_4$ | H | OCH$_3$ | CH$_3$ | O | CH | |
| 5.44 | Q$_4$ | H | OCH$_3$ | OCH$_3$ | O | CH | |
| 5.45 | Q$_4$ | H | CH$_3$ | OCHF$_2$ | O | CH | |

Example 3

Formulation examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |

-continued

| (a) Wettable powders | (a) | (b) | (c) |
|---|---|---|---|
| sodium diisobutylnaphthalene-sulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4-5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |

| (f) Suspension concentrate | (a) | (b) |
|---|---|---|
| 37% aqueous formaldehyde solutions | 0.2% | 0.2% |
| silocone oil in the form of a 75% aueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glykol ether (78 moles of ethylene oxide) | 3% |
| water | 91% |

BIOLOGICAL EXAMPLES

Example 4

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 lux and a relative humidity of 70%. During the germinating phase of 4 to 5 days, the pots are covered with light-permeable material and watered with deionised water to increase the local humidity. After the 5th day, 0.5% of a commercial liquid fertilizer (Greenzit ®, ex Ciba Geigy) is added to the water. The test is evaluated 12 days after sowing and the action on the plants is assessed according to the following rating:

1: plants have not emerged or are totally withered
2-3: very pronounced action
4-6: medium action
7-8: weak action
9: no action (as untreated controls).

Preemergence action:
Concentration of the test compound emulsion: 70.8 ppm

| | Test plant | | | |
|---|---|---|---|---|
| Compound | Nasturtium | Stellaria | Agrostis | Digitaria |
| 5.1 | 1 | 1 | 1 | 1 |
| 5.3 | 2 | 2 | 1 | 2 |
| 5.4 | 2 | 2 | 1 | 2 |
| 5.5 | 2 | 2 | 1 | 2 |
| 5.7 | 1 | 2 | 1 | 2 |
| 5.8 | 2 | 2 | 1 | 2 |
| 5.9 | 2 | 2 | 1 | 2 |
| 5.10 | 2 | 2 | 1 | 2 |
| 5.11 | 2 | 2 | 1 | 2 |
| 5.12 | 2 | 2 | 1 | 2 |
| 5.13 | 2 | 2 | 1 | 2 |
| 5.19 | 2 | 1 | 1 | 2 |

Example 5

Growth inhibition of tropical cover crops

The test plants (*Centrosema plumieri* and *Centrosema pubeseens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

What is claimed is:

1. A phenylsulfonamide of the formula II

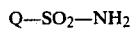  (II), wherein
Q is selected from

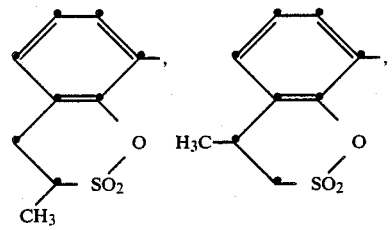

2. A phenylsulfonylisocyanate or phenylsulfonylisothiocyanate of the general formula IV

  (IV), wherein
Q is selected from

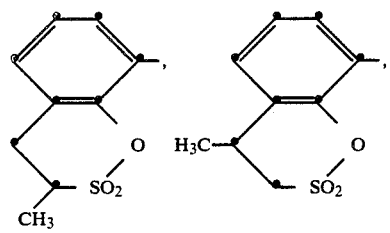

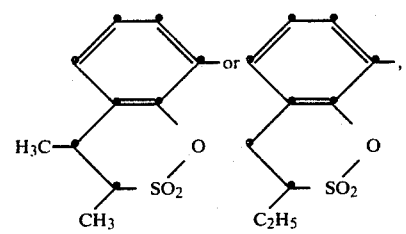

and
Z is oxygen or sulfur.

3. A phenylsulfonylcarbamate of the formula VI

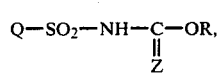  (VI)

wherein
Q is selected from

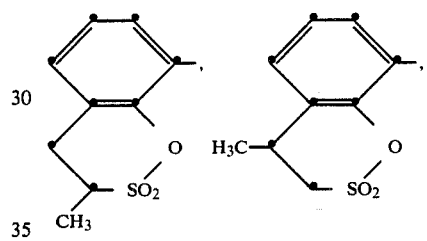

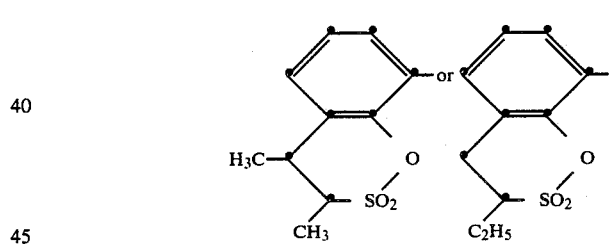

Z is oxygen or sulfur, and R is phenyl, alkyl or substituted phenyl.

4. A phenylsulfonyl chloride of the formula X

  (X), wherein
Q is selected from

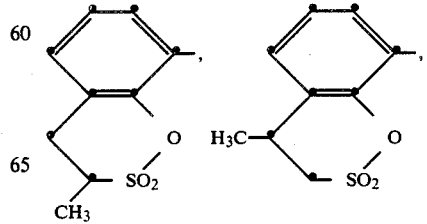

-continued
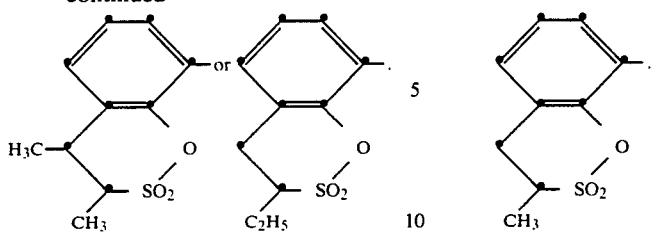
5. A compound according to claim 1, wherein Q is
* * * * *